United States Patent [19]

Sting et al.

[11] Patent Number: 5,051,602
[45] Date of Patent: Sep. 24, 1991

[54] OPTICAL SYSTEM AND METHOD FOR SAMPLE ANALYZATION

[75] Inventors: Donald W. Sting, New Canaan; Robert G. Messerschmidt, Westport; John A. Reffner, Stamford, all of Conn.

[73] Assignee: Spectra-Tech, Inc., Stamford, Conn.

[21] Appl. No.: 627,730

[22] Filed: Dec. 14, 1990

Related U.S. Application Data

[62] Division of Ser. No. 487,550, Mar. 2, 1990.

[51] Int. Cl.$^5$ ............................................. G01N 21/86
[52] U.S. Cl. ..................................... 250/571; 250/216; 250/237 G; 356/445
[58] Field of Search ................ 250/216, 237 G, 571, 250/572; 350/525, 620, 622; 356/317–319, 445–448

[56] References Cited

U.S. PATENT DOCUMENTS

| | | | |
|---|---|---|---|
| 3,930,713 | 1/1976 | Stankewitz et al. | 350/525 |
| 3,958,882 | 5/1976 | Gast | 356/445 |
| 3,963,354 | 6/1976 | Feldman et al. | 250/572 |
| 4,050,895 | 9/1977 | Hardy et al. | 356/445 |
| 4,062,623 | 12/1977 | Suzuki et al. | 356/445 |
| 4,127,318 | 11/1978 | Determann et al. | 350/525 |
| 4,176,964 | 12/1979 | Knör et al. | 250/571 |
| 4,377,340 | 3/1983 | Green et al. | 356/237 |
| 4,439,012 | 3/1984 | Christy | 350/620 |
| 4,449,818 | 5/1984 | Yamaguchi et al. | 250/572 |
| 4,655,592 | 4/1987 | Allemand | 350/622 |
| 4,878,747 | 11/1989 | Sting et al. | 350/511 |

Primary Examiner—David C. Nelms
Assistant Examiner—S. B. Allen
Attorney, Agent, or Firm—Calfee, Halter & Griswold

[57] ABSTRACT

An optical system, apparatus and method for analyzing samples includes a radiant energy source, a first mask, a first mirror system, a sample plane, a second mirror system, a second mask and a detector. The first and second masks are respectively positioned along the optical path of the system in the same or different Fourier planes and/or conjugate planes thereof. The first mask has at least one inlet aperture with the relative position thereof in the first mask determining the angle of the energy incidence onto the sample. The second mask has at least one outlet aperture therein passing radiant energy therethrough which has been reflected from or transmitted through the sample at a preselected angle determined by the relative position of the second aperture in the second mask. Numerous first and second masks respectively having inlet and outlet apertures at different radial and/or circumferential positions may be used in the optical system to perform many types of analyses without moving or specially preparing the sample.

4 Claims, 4 Drawing Sheets

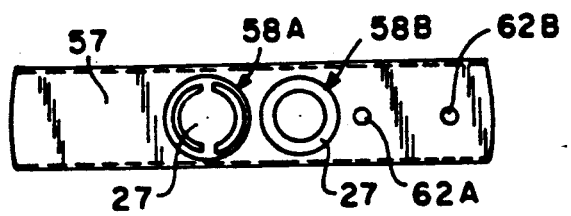
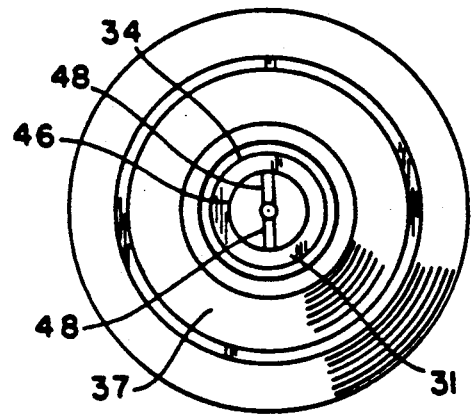
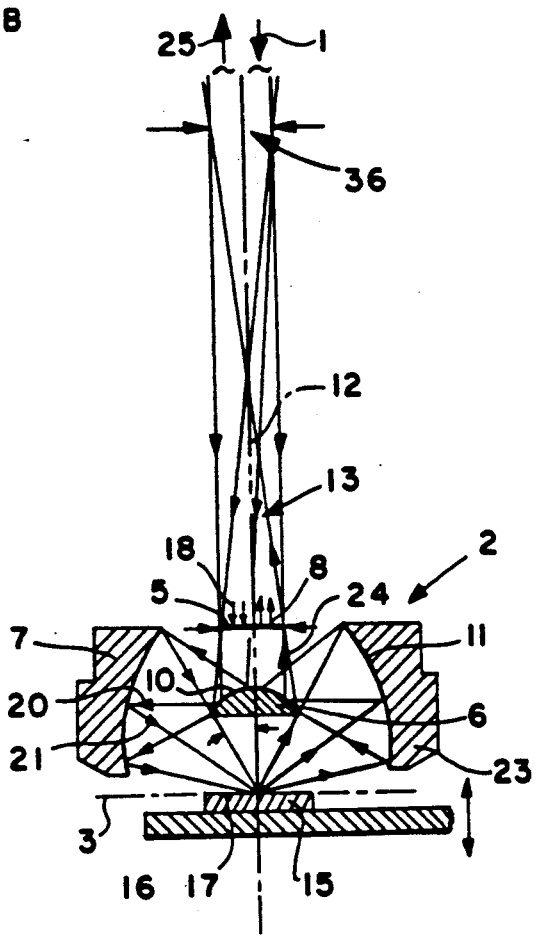
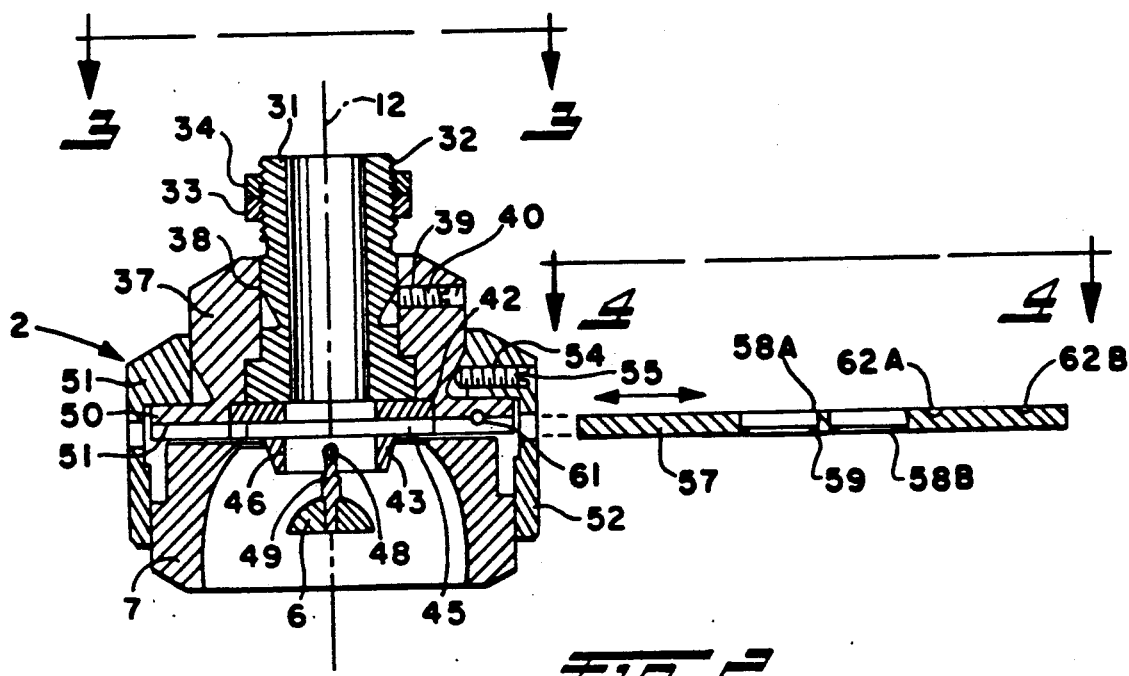

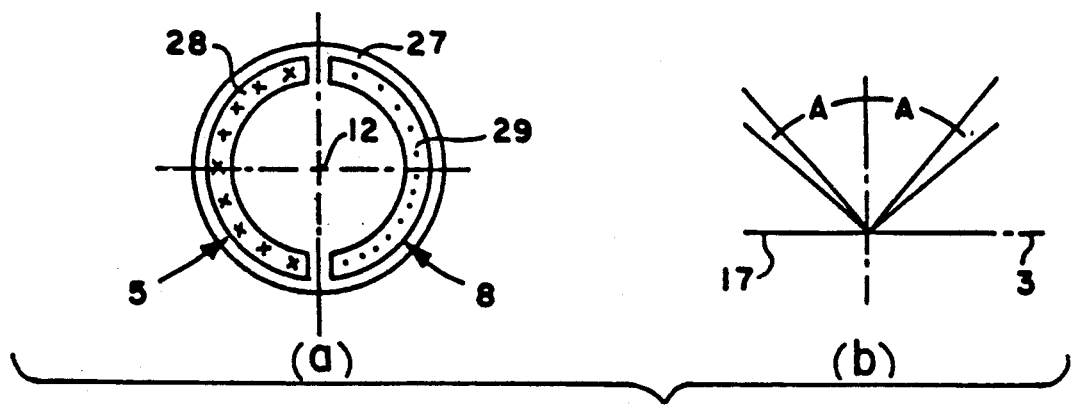
Fig. 7A1
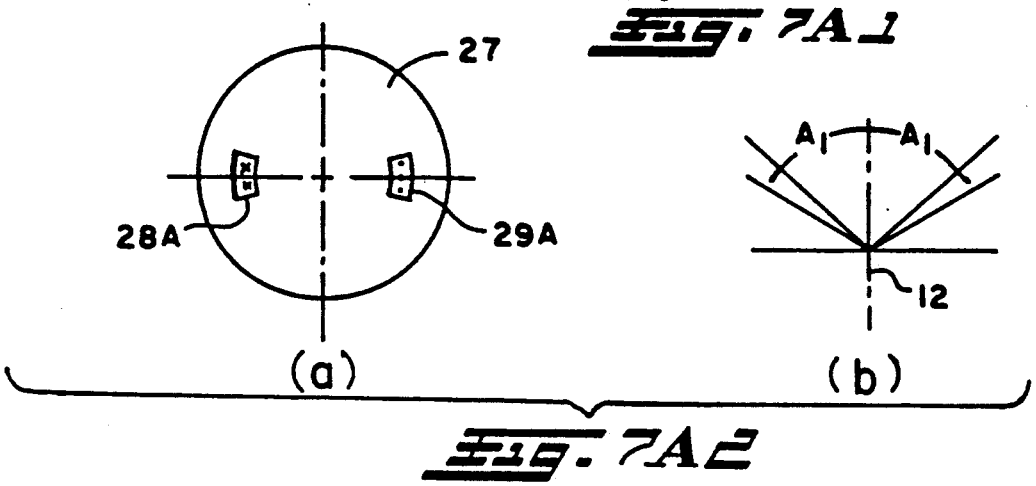
Fig. 7A2
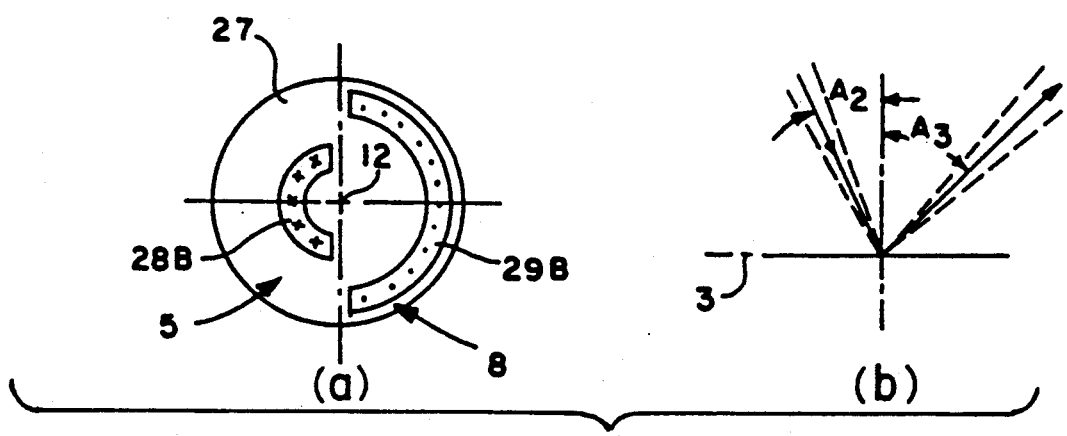
Fig. 7B1
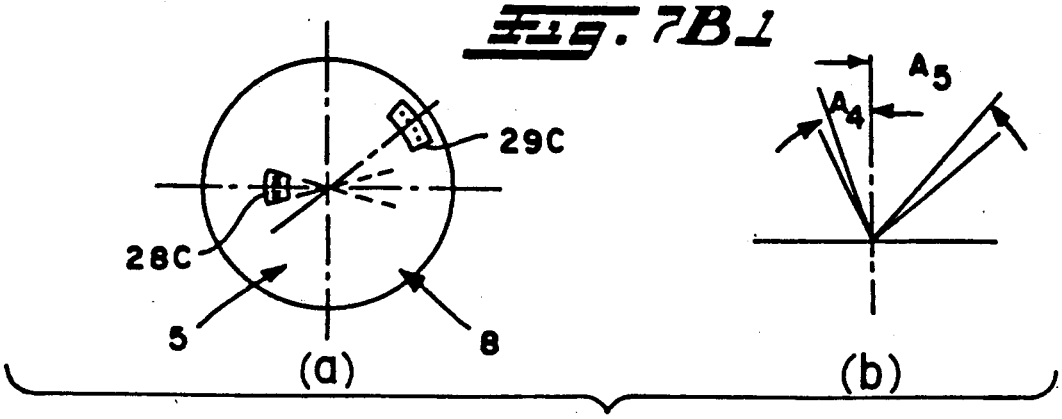
Fig. 7B2

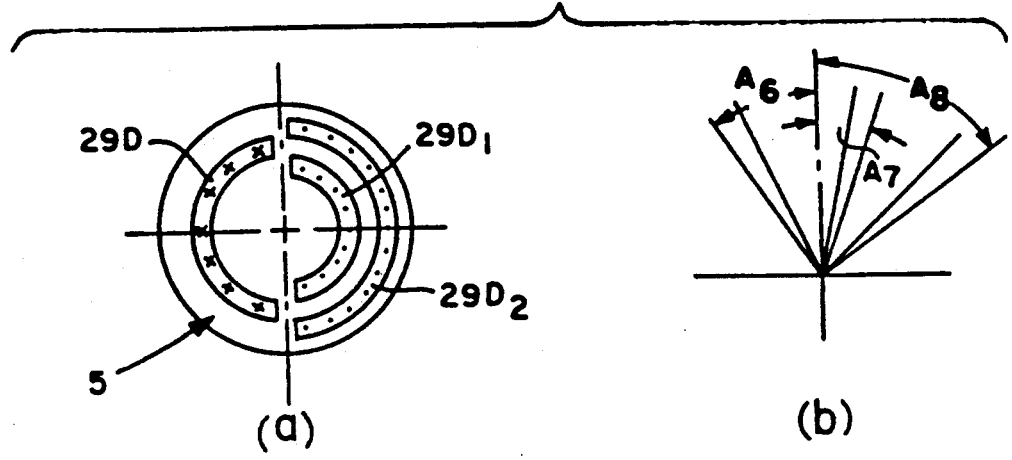
Fig. 7C1
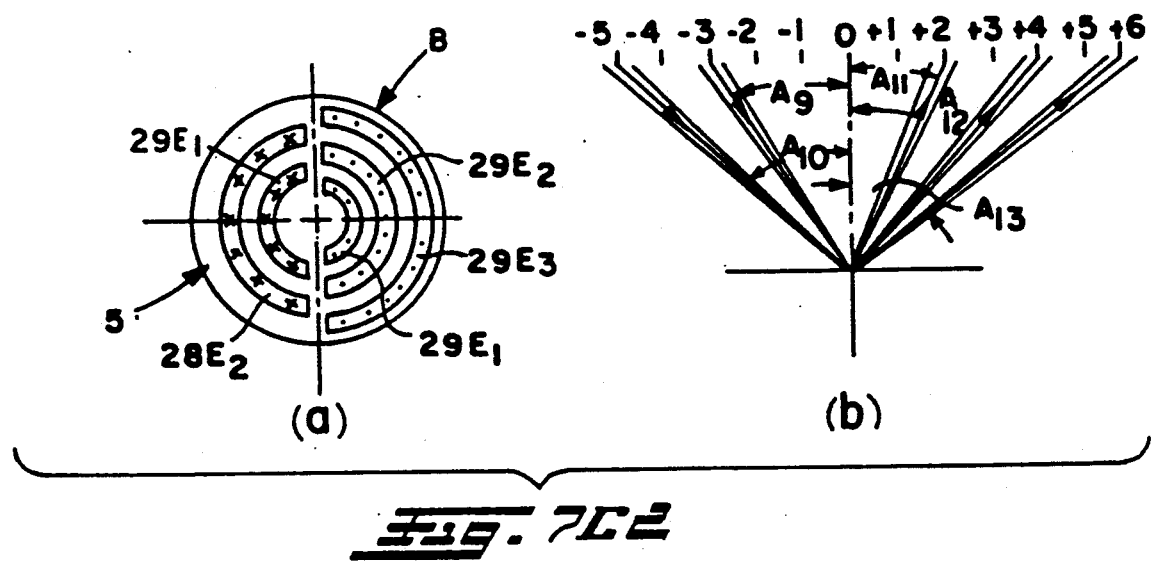
Fig. 7C2

OPTICAL SYSTEM AND METHOD FOR SAMPLE ANALYZATION

This is a division of application Ser. No. 07/487,550 filed Mar. 2, 1990.

FIELD OF THE INVENTION

The present invention relates, in general, to an optical spectroscopy system and method and, in particular, to an optical system and method utilizing inlet and outlet masks at a Fourier plane of the optical system to enhance optical spectroscopy procedures.

BACKGROUND OF THE INVENTION

Optical spectroscopy is widely used for various analytical techniques and for experimental techniques in applied and basic research. Experiments utilizing spectroscopy are performed to determine optical constants of material samples as well as to establish the chemical and physical composition of those material samples. However, optical spectroscopy, particularly in the mid-infrared energy region, is still limited by: (1) sensitivity of the detectors utilized which have a comparatively small dynamic range; (2) anomolies resulting from surface variations and/or inhomogenities; and (3) changes in the indices of refraction which appear to change the absorbtiveness of the sample materials.

In the past, various spectroscopic apparatus has been developed to vary certain parameters to determine the optical constants of a material by the variations detected. Alternatively, spectroscopic techniques have been used to determine absorbtivities of materials. In fact, libraries of books and electronic media exist which uniquely identify pure materials by means of their absorbtions of electromagnetic radiations at various frequencies.

Unfortunately, the resulting spectra derived by the use of current spectroscopic apparatus or spectroscopic sampling techniques typically require that the materials be analyzed in a form which requires extensive sample preparation or even sample destruction. Such sample preparation normally utilizes a sealed cell or a KBR pressed technique. In addition, current spectroscopic apparatus may require the sample to be moved from instrument to instrument in order to obtain the full range of spectroscopic tests required. Alternatively, the instrument used may have to be temporarily modified to utilize additional peripheral or optional equipment to perform the full range of spectroscopic analysis. The sample preparation and variations in equipment require additional time to be expended to obtain the spectroscopic analysis results and may adversely effect those results due to the partial or total destruction of the sample and/or to the variations between equipment.

SUMMARY OF THE INVENTION

The present invention provides an optical system, apparatus and method to more readily and accurately determine the optical constants, absorbtivities and/or refractice indices of a material. This system, apparatus and method employ a first or inlet mask at a Fourier plane of the optical system and a second or outlet mask at a Fourier plane of the optical system. The relative position of the respective inlet and outlet apertures in the first and second masks, respectively, controls the angle of energy incidence onto the sample and also controls the angle of reflected or transmitted energy that reaches the detector. Multiple first and second masks respectively having first and second apertures of varying radial and/or circumferential position may be employed to perform a wide range of spectroscopic analyses. In a preferred form of the present invention, the angles of incident radiant energy onto the sample may be varied from approximately 30° up to and including grazing angles of approximately 85°. A similar range of angles may be obtained for the reflected and/or transmitted energy selectively reaching the detector by passing through the second mask.

The optical system, apparatus and method enhance the detectivity of small amounts of sample material or special characteristics of a material. The enhanced detectivily characteristic is provided by being able to accurately target the incident energy reaching the sample at preselected angles of incidence and to accurately collect and detect that energy reflected or transmitted from the sample at preselected angles of reflectance or transmission. In addition, by being able to accurately and quickly change inlet and outlet masks having various inlet and outlet aperture positions, various studies may be rapidly performed on a stationary sample which does not require special preparation and/or destruction.

The preferred apparatus of the present invention includes an objective assembly incorporating a Cassegrain mirror objective and a Fourier plane mask and slide. This objective assembly may be readily attached to one section or station of a rotatable microscope nosepiece. The objective apparatus includes adjustment means for centering the objective relative to the center line of the optical path and/or to move the primary mirror of the objective relative to the secondary mirror. In addition, the mask slide may include a plurality of receptacles respectively receiving a plurality of different masks allowing the masks to be quickly and accurately changed.

By utilizing a Fourier plane or a conjugate of the Fourier plane for masking the optical path, the present optical system, apparatus and method is able to reduce the anamolies associated with surface irregularities and/or inhomogenities and provides spectra allowing materials to be more accurately identified by spectral library searches. In addition, this system, apparatus and method can be used more accurately to identify materials in a mixture and to quantify those materials as a percentage of that mixture.

These and other objects and advantages of the present invention will become apparent as the following description proceeds.

DESCRIPTION OF THE DRAWINGS

FIG. 1 is a schematic elevation, partially in section, showing the optical system of the present invention set up for performing reflectance analyses;

FIG. 2 is a vertical cross section showing the details of the preferred objective assembly with the mask slide positioned for telescopic insertion;

FIG. 3 is a plan view of the objective assembly taken generally along the plane 3—3 in FIG. 2;

FIG. 4 is a plan view of the mask slide taken generally along the plane 4—4 of FIG. 2;

FIG. 7A illustrates two exemplary sets of inlet and outlet masks for specular reflective analysis of a sample material;

FIG. 7B illustrates two exemplary sets of inlet and outlet masks for performing dark field or scatter reflectance analysis of the sample material; and FIG. 7C illustrates two exemplary sets of multiple band apertures for inlet and outlet masks to perform dark field or scatter analysis of the sample material.

DETAILED DESCRIPTION OF THE PREFERRED EMBODIMENT

Figures 5, 6:
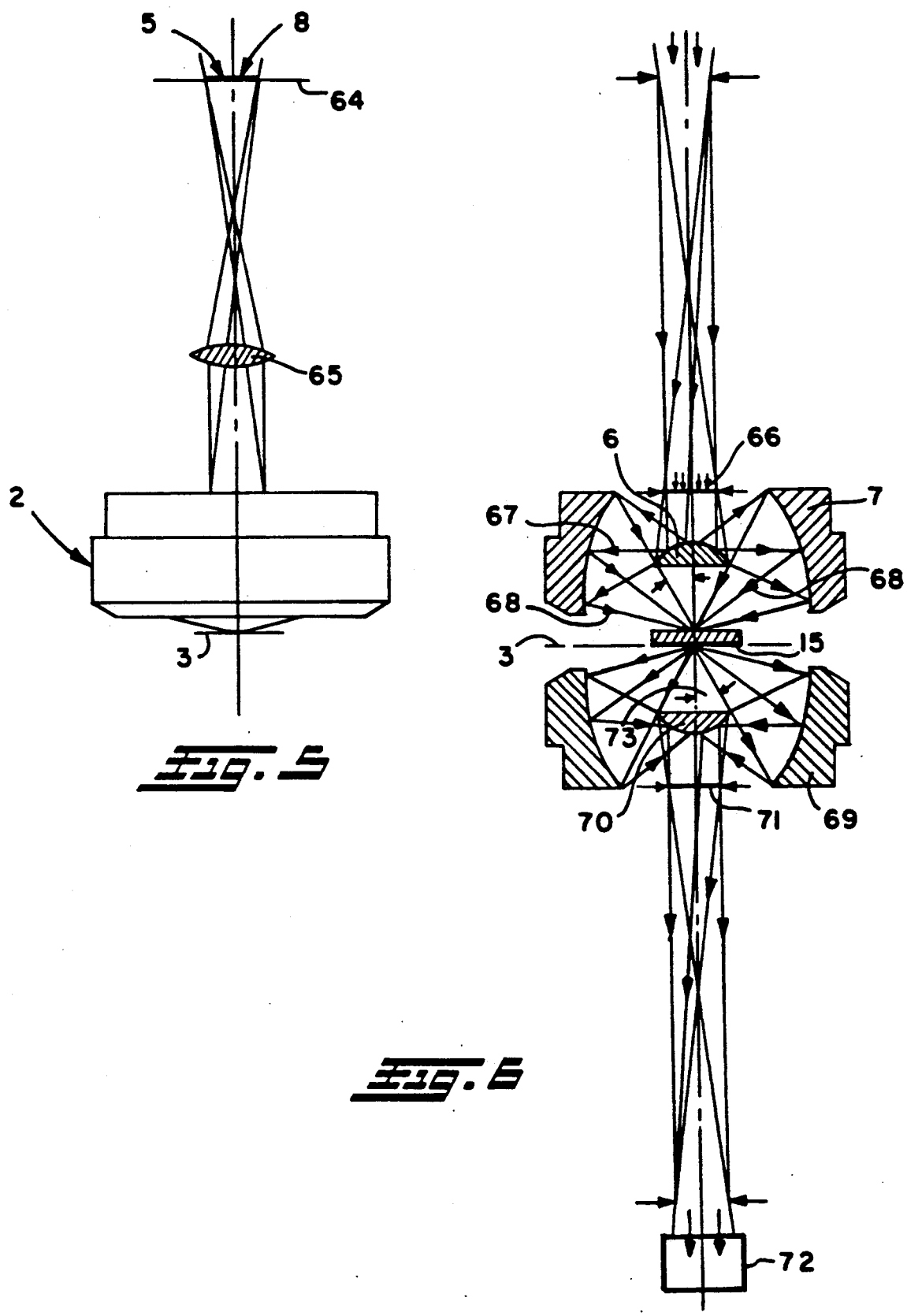
FIG. 5 is a schematic elevation of the optical system of the present invention, wherein the inlet and outlet masks are positioned at a conjugate plane of the Fourier plane of the optical path.
FIG. 6 is a schematic elevation partially in section showing the optical system of the present invention set up for performing full field transmissive analayses of the sample material.

Turning now in more detail to the invention and initially to FIG. 1, the optical system includes a radiant energy source, indicated generally at 1, an objective assembly, indicated generally at 2, and a sample plane 3. The objective assembly 2 includes a first mask 5, a secondary optic 6, a primary optic 7 and a second mask 8. The secondary optic 6 has a convex mirror surface 10, and the primary optic 7 has a truncated, concave mirror surface 11. Primary mirror 11 optically cooperates with and is spaced from secondary mirror surface 10. Secondary mirror 10 and the primary mirror 11 are coaxial to and symmetric about the center line 12 of the optical path, which is indicated generally at 13. Secondary mirror 10 of secondary optic 6 and primary mirror 11 of primary optic 7 cooperate to form a Cassegrain mirror objective.

A sample 15 may be positioned in the optical path 13 of the optical system by a positioned stage or support 16. A surface 17 of the sample 15 is positioned in the sample plane 3 of the optical system. With the sample in that temporarily fixed position, the optical system of the present invention may be utilized to perform a plurality of optical or spectroscopic tests on the sample without specially preparing the sample and without moving the sample.

The source of radiant energy provides a beam of radiant energy, preferably in the mid-infrared range. As illustrated in FIG. 1, the optic system is utilizing a "half aperture" of the radiant beam for this spectrascopic analysis. For this purpose, a beam splitter is utilized to direct only half of the beam to the inlet of the objective assembly, as schematically illustrated by arrows 18. For this beam splitting purpose, an aperture image beam splitter can be utilized, for example, as shown in U.S. Pat. No. 4,878,747, which is owned by the assignee of the present invention.

The half beam of radiant energy selectively passes through the apertures in the inlet or first mask 5 of the objective assembly 2. The inlet mask 5 is positioned at or near a Fourier plane of the optical system. For purposes of the present application, a Fourier plane is defined as a plane having the property that the radial position that a ray intersects that plane has a directly correlated function, normally linear, to the angle of incidence or reflection that the ray will have with the sample plane after passing from or to the objective.

Inlet radiant energy passing through an aperture in first mask 5 on one side of the optic center line 12 will sequentially reflect off secondary mirror 10 and primary mirror 11, as schematically indicated by arrows 20 and 21, respectively. The incident radiant energy reflected from primary mirror 11 is directed toward the sample surface 17 of sample 15. The incident radiant energy will strike the sample surface 17 at or very closely adjacent the intersection of the center line 12 with that sample plane 3. The angle of incidence for the energy is defined as the included angle between the incident radiant energy beam and the optical center line 12. The incident angle for the radiant energy onto the sample may be varied by utilizing a plurality of different inlet masks 5 at the Fourier plane, as will be described in more detail hereinafter.

The radiant energy reflected from sample surface 17 sequentially reflects off primary mirror 11 and second mirror 10, as schematically indicated by the arrows 23 and 24, respectively. Output energy reflected from secondary mirror 10 moves along the optical path 13 to second mask 8, positioned at the Fourier plane. Selected radiant output energy passes through the aperture or apertures in second mask 8 to a detector, indicated generally at 25. By varying the radial and/or circumferential position of the apertures in second mask 8, the detector 25 will only receive radiant energy being reflected from the sample surface 17 at preselected angles of reflectance, because such second mask and the aperture(s) therein are positioned in or near a Fourier plane of the optical system.

The utilization of a plurality of first and second masks at a Fourier plane provides significant spectroscopic versatility without moving the sample in plane 3 or changing instruments. As best shown in FIGS. 7A through 7C, a plurality of different first and second masks 5 and 8, respectively, can be utilized for different types of spectroscopic analyses.

Turning first to FIG. 7A(1), the inlet mask 5 and outlet mask 8 may be commonly formed on a single disc body 27. The first mask 5 on the left semicircle of disc body 27 as viewed in FIG. 7A(1)(a), includes a first or inlet arcuate aperture 28 passing therethrough. The radius of first aperture 28 about center line 12 of the optical path has a direct correlation to the desired angle of incidence onto the sample surface 17 because of the direct correlation between the radial position of the ray in the Fourier plane to the angle of incidence of that ray at the sample plane.

As shown in FIG. 7A(1)(a), the first arcuate aperture 28 is substantially semi-circular in its extent. The first aperture 28 has a limited width along its entire semi-circular extent. This limited width allows a limited semicircular band of inlet radiant energy to pass therethrough as indicated by the "Xs" in FIG. 7. The band of inlet energy passing through first aperture 28 is reflected through the Cassegrain objective and is then accurately targeted onto the sample surface at the sample plane at the preselected angle of incidence.

The second mask 8 constitutes the right semi-circular portion of disc body 27. This second mask 8 includes a semi-circular second or outlet aperture 29. The second aperture 29 has a limited width to allow selected outlet or reflected radiant energy to reach the detector as indicated by the "dots" in FIG. 7. For specular reflectance studies, the radius of the second aperture 29 from the center line 12 of the optical path 13 is equal to the radius from that center line for the first aperture 28. The second aperture 29 also has a width which is equal to the width of first aperture 28 in first mask 5.

When the masks 5 and 8 are positioned in or near a Fourier plane of the optical system, first aperture 28 in first mask 5 and the second aperture 29 in second mask 8 will permit specular reflectance studies to be performed. The radial position of first aperture 28 from the center line 12 determines the angle of the incident radiant energy onto the sample plane 3. Similarly, the radius of the second aperture 29 from the center line 12 controls the angle of reflectance for reflected radiant energy which will ultimately pass through aperture 29 to reach the detector 25. With equal radii for the first and second apertures, the angle of incidence A will equal the angle of reflectance A, as shown in FIG. 7A(1)(b).

Other types of specular reflectance studies can be performed by utilizing different masks. For example, in FIG. 7A(2)(a), the disc body 27 again has an inlet or first mask 5 on the left semi-circular portion thereof and the second or outlet mask 8 on the right semi-circular portion thereof. The first mask 5 has a first or inlet aperture 28A of circumferentially limited arcuate extent. The radius of arcuate aperture 28A determines the angle of incidence of the incident radiant energy reaching the sample plane. The circumferential extent of the aperture 28A correspondingly limits the circumferential extent of the radiant energy band reaching the sample plane 3.

A second or outlet aperture 29A of equally limited arcuate extent is provided in second mask 8. This outlet aperture 29A controls the reflected radiant energy that may pass therethrough to the detector 25. The radius of second aperture 29A in second mask 8 is equal to the radius of the first or inlet aperture 28A in first mask 5. With such equal radii, the angle of incidence A1 of the radiant energy on the sample plane equals the angle of reflection A1 for the radiant energy which will pass through the second mask 8 to the detector. The disc body 27 having the limited inlet and outlet apertures 28A and 29A, respectively, can be rotated from time to time to check specular reflectance characteristics at other circumferential points around the optical energy path. Similarly, the first and second masks 5 and 8 could be formed as individual semi-circular bodies for selective utilization with one another.

If non-specular or scatter type reflectance studies are desired, different inlet and outlet aperture configurations and radial positions can be utilized in the inlet and outlet masks, as shown for example in FIGS. 7B and 7C. Initially referring to FIG. 7B(1), the inlet aperture 28B in first mask 5 is substantially semi-circular in its extent and has a limited radius from the center line 12 of the optical path. Inlet energy passing through first aperture 28B will have an angle of incidence A2 onto the sample surface 17 at sample plane 3, as shown in FIG. 7B(1)(b). The second outlet aperture 29B in outlet mask 8 is also substantially semi-circular in its extent. The radius of outlet aperture 29B from the center line 12 is shown greater than the radius for the first aperture 28B from center line 12. Since both the first and second apertures 28B and 29B are positioned at a Fourier plane, the angle of reflectance A3 for radiant energy leaving sample plane 3 which will pass through second aperture 29B to detector 25 is greater than the angle of incidence A2. Therefore, the radius of second aperture 29B is selected to ultimately detect radiant energy reflected from the sample at a predetermined angle of "scattered" reflectance A3. It will be understood that the radius of 29B could be either greater than or less than the respective radius of 28B depending upon the desired angles of scattered energy to be collected.

Another example of masks which may be utilized for scatter reflectance analysis is shown in FIG. 7B(2). In such example, the inlet or first aperture 28C in first mask 5 is of limited circumferential extent and has a relatively small radius of curvature about center line 12 of the optical path. The second or outlet aperture 29C is also of limited circumferential extent but is not diametrically opposed to inlet aperture 28C. Instead, second aperture 29C in outlet mask 8 has a greater radius about center line 12 than the radius for arcuate inlet aperture 28C and is circumferentially offset relative thereto. With first aperture 28C and second 29C positioned as shown, the angle of incidence for energy reaching the sample plane is shown in FIG. 7B(2)(b) as A4, while the angle of reflectance for energy reaching the detector is A5. The angle of reflection A5 is greater than the angle of incidence A4, and the energy reaching the detector is both scattered and deflected relative to the inlet energy. As will be appreciated, the inlet aperture 28C and outlet aperture 29C can be both radially and circumferentially varied relative to one another, as required for the analysis desired.

Turning now to FIG. 7C, additional masks are shown for doing dark field or scatter type reflectance analysis wherein numerous apertures are utilized in the inlet and outlet masks. Turning first to FIG. 7C(1) inlet mask 5 has semi-circular inlet aperture 28D. The outlet mask 8 has two energy outlet apertures 29D1 and 29D2. The radius of inlet aperture 28D about center line 12 is greater than the radius for outlet aperture 29D1 and less than the radius for outlet aperture 29D2. With such relative positioning of inlet aperture 28D and outlet apertures 29D1 and 29D2, the angle of incidence A6 for energy reaching sample plane 3 through aperture 28D is greater than the angle of reflectance A7 for energy reaching the detector through outlet aperture 29D1 and less than the angle of reflectance A8 for the reflected energy reaching the detector 25 through outlet aperture 29D2.

In FIG. 7(C)(2) multiple inlet and outlet apertures are illustrated. Specifically, the inlet mask 5 has a first inlet aperture 28E1 and a second inlet aperture 28E2. The radius of inlet aperture 28(E)(1) about the center line 12 of the optical path is less than the radius of inlet aperture 28E2 in inlet mask 5. Incoming radiant energy passing through first inlet aperture 28E1 will have an angle of incidence A9 onto the sample plane 3. Incoming radiant energy passing through second inlet aperture 28E2 will have an angle of incidence A10 onto the sample plane 3.

In the outlet mask 8, three semi-circular outlet apertures 29E1, 29E2 and 29E3 are provided. The radius for outlet aperture 29E1 is less than the radius for outlet aperture 29E2, which in turn is less than the radius for third outlet aperture 29E3. As is apparent from FIG. 7C(2)(a) the radius of inlet aperture 28E1 has a magnitude halfway between the radii for outlet apertures 29E1 and 29E2 and the radius of inlet aperture 28E2 has a magnitude halfway between the radii for outlet apertures 29E2 and 29E3. As a result of the relative magnitudes of the respective radii of the inlet and outlet apertures in the inlet and outlet masks, the angle of reflectance A11 for energy reaching the detector through outlet aperture 29E1 is less than the angle of incidence A9. Similarly, the angle of reflection A12 for energy reaching the detector through second outlet aperture 29E2 is greater than the angle of incidence A9 but less than the angle of incidence A10. Finally, the angle of reflectance A13 for reflected energy reaching the detector through outlet aperture 29E3 in outlet mask 8 is greater than the angle of incidence A10 for energy reaching the sample surface through inlet aperture 28E2.

The inlet and outlet masks shown in FIGS. 7A-7C are merely exemplary of the many different mask configurations that may be used with the present invention. By varying the radial position of the inlet apertures in the inlet mask, the angle of incidence for the radiant energy reaching the sample can be varied from 30° to 85° for the Cassegrain objective illustrated. These masks need to be accurately positioned in the optical path at or near a Fourier plane of the optical system. For this purpose, an objective assembly has been developed and is illustrated in FIGS. 2-4.

Referring initially to FIG. 2, the objective assembly 2 includes a microscope connecting tube 31. The outer diameter of the connecting tube 31 at its upper end is provided with threads 32. These threads mate with threads on one of the stations of a rotatable microscope nosepiece. The connecting tube is threaded into the microscope nosepiece station until properly positioned and held in place by jam nut 33 and lock nut 34. The radiant energy of the optical path 13 passes through the bore of the connecting tube 31. The jam and lock nuts properly position the objective assembly 2 in the optical path of the microscope to establish the proper predetermined distance between the field stop of the optical system, indicated generally at 36, and the sample plane 3.

A guide holder 37 is positioned around and supported by connecting tube 31. A bore 38 through the guide holder body 37 receives the connecting tube 31. The guide holder 37 has a tapped hole 39 radially passing therethrough. A first optic centering screw 40 is threadedly received in tapped hole 39. This centering screw 40 provides some radial adjustment for the guide holder 37 relative to the center line 12 of the optical system.

The bottom end of guide holder 37 has a bottom counter bore 42. This counter bore 42 receives a slide guide 43, which is fixedly secured thereto. The slide guide has a longitudinal slide slot 45 extending diametrically therethrough. A center bore 46 extends through the slide guide body, with such bore being concentric with the center line 12 of the optical system to pass radiant energy therethrough.

The secondary optic 6 is mounted to and suspended from the slide guide 43. For this purpose, mounting spider 48 extends diametrically inwardly from the center bore 46 of slide guide 43 and is connected to mounting pin 49 of secondary optic 6 to support that secondary optic in the optical path. By being diametrically oriented and properly positioned, the mounting spider 48 support the secondary optic 6 in the optical path without significantly interferring with the effective input and output of radiant energy to and from the objective assembly 2. In this regard, the mounting spider 48 define semi-circular windows on either side thereof consistent with the semi-circular shape of the inlet and outlet masks used for reflectance type studies in the preferred embodiment.

The bottom of guide holder 37 has a radially outwardly extending annular flange 50 thereon. The bottom wall 51 of flange 50 is horizontally aligned with the top surface of slot 45 to provide radial access to such slot. The flange 50 also provides support for a rotatable outer ring or collar 51.

The outer ring 51 includes a downwardly extending annular skirt 52, which has a threaded internal diameter. The primary optic 7 is received within annular skirt 52 on outer ring 51. The outer diameter of primary optic 7 has threads thereon to cooperate with the threads on the internal diameter of skirt 52. Therefore, rotation of the outer collar 51 will, depending upon direction of rotation, either raise or lower the primary optic 7 because of the threaded connection therebetween. This elevational adjustment of the principal optic 7 may be used to obtain the proper spacial relationship between the primary optic 7 and the secondary optic 6 for the tests being performed.

To provide further adjustment of the objective relative to the center line of the optical path, outer ring 51 has a threaded hole 54 passing radially through its upper end. Threaded hole 54 receives the second and primary optic centering screw 55. Radial advancement or withdrawal of the primary centering screw 55 can radially adjust the position of the primary optic 7 relative to the secondary optic 6 to obtain proper centering around the optical center line 12 of the microscope.

With the objective assembly 2 secured to the rotatable microscope nose piece and with the optic adjustments properly made, the guide slot 45 is positioned on a Fourier plane of the optical system. A mask slide 57 may be radially inserted into and withdrawn from slot 45 in slide guide 43. Such mask slide 57 has an elongated rectangular shape, as best shown in FIG. 4. The width of mask slide 57 substantially equals the width of guide slot 45 to provide a relatively tight sliding fit therebetween.

The mask slide 57 has two (or more) circular receptacles 58A and 58B therein. As best shown in FIG. 2, each of these receptacles includes a bore passing entirely through mask slide 57. The bore of each receptacle has a bottom lip 59 protruding slightly radially inwardly relative to the bore to provide support for the inlet and outlet masks. In this regard, inlet and outlet masks 5 and 8 respectively having inlet aperture 28 and outlet aperture 29, as shown in FIG. 7A(1) are inserted in the receptacle 58A by placing the disc 27 into the bore. Such disc is supported in the receptacle 58A by lip 59. A second disc 27 may be similarly inserted in second receptacle 58B. As shown, the disc 27 in second receptacle 58D has a circular aperture therein for visual viewing purposes with visible light. Alternatively, another mask disc of the type shown in FIG. 7A through 7C could be inserted into receptacle 58B. One of the two receptacles may be properly centered in the optical system at a Fourier plane thereof by suitable locator means.

For example, the bottom surface 52 of flange 50 may be provided with a partially exposed spring loaded ball 61. This ball is in centered radial alignment with the center of the guide slot 45. The slide may be inserted through the hole in the skirt of outer ring 51 with the ball 61 being cammed into retracted position to allow such insertion. The slide 57 will be temporarily stopped when the spring loaded ball 61 is received in a correspondingly configured detent 62A on the top surface of mask slide 57. When the ball 61 is received in detent 62A, the first receptacle 58A is centered on the center line 12 of the optical path of the system.

A second detent 62B is provided in the top surface of mask slide 57 in longitudinal alignment with but spaced from the first detent. When the spring loaded ball 61 is received second detent 62B, the second receptacle 68B is centered on the center line 12 of the optical path of the system. By adjusting the radial position of mask slide 57, one of two mask discs can be centered with the optical system without making any adjustments to or changes on the instrument and without moving the sample. Still further studies can be performed by withdrawing the slides changing the mask discs in the first and second receptacles of the slide 57 and then reinserting the same into the optical assembly 2. This objective assembly 2 can be used with different optical masks and/or paths for the same or different types of spectroscopic analysis.

For example, as shown in FIG. 5, the inlet mask 5 and outlet mask 8 may be positioned in a conjugate plane 64 of the Fourier plane when access to the Fourier plane is difficult or greater size is required. A lens 65 (preferably a mirror system for FTIR use) may be inserted in the optical system to create a real image at the conjugate plane 64 of the Fourier plane for the optical system.

FIG. 6 discloses another optical path utilizing the present invention for transmissive spectroscopic studies. The optical system of FIG. 6 employs the full aperture or field of the radiant energy by eliminating the beam splitter. Thus, the first mask 66 may utilize the entire circular disc body 27. Any aperture placed anywhere in that circular disc body will act to pass radiant energy into the system and will control the angle of incidence of that incoming energy onto the sample 3. The arrows 67 and 68 schematically illustrate potential incoming energy patterns onto the sample surface 3.

A like or similar optical system is positioned on the other side of the sample plane 3 to collect energy transmitted through the sample 15. The optical collector system includes a primary optic 69, a secondary optic 70, a second mask 71, and a detector 72. The second mask 71 is positioned at a Fourier plane of the optical collector system.

The second mask 71 of the transmission analysis path of FIG. 6 is also a full aperture or field. Therefore, the entire circular extent of the mask disc may be utilized for desired outlet aperture configurations and radial positioning. The position of the apertures in the second mask 71 controls the angle of transmission or acceptance 73 for energy transmitted through sample 15 which will ultimately reach detector 72 by way of the objective and the apertures in second mask 71. In this regard, radiant energy transmitted through sample 15 will sequentially reflect off primary optic 69 and secondary optic 70 and will then pass through the aperture or apertures in second mask 71 to reach detector 72. Obviously, the configuration of the inlet and outlet apertures in inlet and outlet masks 67 and 71, respectively, may be varied to control the angle of incidence onto the sample and to control the angle of transmission or acceptance from the sample to the detector. Many different masks may be used in this radiant transmission system to perform a number of spectroscopic transmissive studies.

The various tests or analyses that can be run on a single sample utilizing multiple masks positioned at the Fourier plane for the selected mode of transmission, reflectance or emission are compared to one another at the detector to determine the differences therebetween. The differences obtained are then utilized in conjunction with known mathematical algorithms (for example, Kramer's Kronig transformation and Kubelka-Munk theory) to more precisely quantify the components of the sample being analyzed and/or to provide for more precise calculation of the sample's optical constants.

As a simple example of this technique, a surface 17 of sample 15 could be subjected to two successive specular reflectance studies performed under the same conditions in the same way. In the first test, the radiant energy could be targeted to the sample by the inlet mask 5 at an angle of incidence of 40°, and the radiant energy reaching the detector through the outlet mask 8 could be collected at an angle of reflection of 40°. A second specular reflectance test would then be run on the same with different inlet and outlet masks (which could be accomplished by merely moving slide 57 to its second position) with the targeted energy set at an angle of incidence of 75° and the collected and detected energy set at at angle of reflection at 75°. The test results are then compared in the context of the test parameters to determine the difference in reflected energy reaching the detector for the two tests. The test parameters and difference obtained are then used in conjunction with known mathematical algorithms to quantify the components of the sample or to determine its optical constants. Many additional specular, transmissive and/or emission studies can be performed on the same sample to enhance the determination being made by utilizing the same comparitive and mathematical techniques.

It will be apparent from the foregoing that changes may be made in the details of construction and configuration without departing from the spirit of the invention as defined in the following claims. For example, the optical system of the present invention can also be used in performing spectroscopic studies on sample materials which partially absorb radiant energy before emitting the same through the incident surface or perform emission studies where the sample is treated as the source of emitted energy.

What is claimed is:

1. An objective system for selectively controlling an aperture of a radiant energy optical path passing therethrough both to and from a sample being analyzed at a sample plane comprising:
   a connecting tube adapted to be removably secured to a sample analysis instrument;
   a guide holder means at least partially surrounding the connecting tube and being supported thereby, the guide holder means having a guide slot therein;
   a secondary optic of a Cassegrain mirror objective supported along the center line of the optical path by the guide holder means;
   an outer ring supported by the guide holder means;
   a primary optic of a Cassegrain mirror objective supported by the outer ring concentrically about the centerline of the optic path and optically cooperating with the secondary optic;
   a slide means slidably received in the guide slot and having at least one receptacle means therein;
   removable mask means at least partially received in the slide receptacle means and being positioned in the optical path at a Fourier plane thereof adjacent the Cassegrain mirror objective when the slide means is properly positioned in the guide slot, the mask means having inlet and outlet apertures, passing radiant energy therethrough at selected radial positions in the Fourier plane to control the incident angle of the radiant energy onto the sample after passage through the objective, the outlet apertures passing radiant energy therethrough at selected radial positions in the Fourier plane to control the angle of reflected or emitted energy travelling from the sample through the objective and outlet apertures to a detector.

2. The optical system of claim 1 further including adjustment means to adjust the objective relative to the center line of the optical path and/or the primary optic relative to the secondary optic.

3. The optical system of claim 1 wherein the removable mask means includes a plurality of masks having different configurations of inlet and outlet apertures to allow a multitude of different analyses to be run on the sample with different angles of incidence being used and different angles of reflection, transmission or emission being detected.

4. The optical system of claim 3 wherein the slide means has multiple spaced receptacle means thereon respectively receiving different masks to allow those masks selectively to be slid into and out of the optical path.

* * * * *